US008236785B2

(12) United States Patent
Coelingh Bennink

(10) Patent No.: US 8,236,785 B2
(45) Date of Patent: Aug. 7, 2012

(54) METHOD OF TREATING OR PREVENTING INFERTILITY IN A FEMALE MAMMAL AND PHARMACEUTICAL KIT FOR USE IN SUCH METHOD

(75) Inventor: Herman Jan Tijmen Coelingh Bennink, Werkhoven (NL)

(73) Assignee: Pantarhei Bioscience B.V., Zeist (NL)

( * ) Notice: Subject to any disclaimer, the term of this patent is extended or adjusted under 35 U.S.C. 154(b) by 466 days.

(21) Appl. No.: 12/522,313

(22) PCT Filed: Jan. 7, 2008

(86) PCT No.: PCT/NL2008/050007
§ 371 (c)(1),
(2), (4) Date: Jul. 7, 2009

(87) PCT Pub. No.: WO2008/085038
PCT Pub. Date: Jul. 17, 2008

(65) Prior Publication Data
US 2010/0113346 A1 May 6, 2010

(30) Foreign Application Priority Data
Jan. 8, 2007 (EP) ..................................... 07100215

(51) Int. Cl.
A01N 45/00 (2006.01)
A61K 31/56 (2006.01)
(52) U.S. Cl. ....... 514/169; 514/170; 514/171; 514/10.2; 514/9.9
(58) Field of Classification Search .................. None
See application file for complete search history.

(56) References Cited

U.S. PATENT DOCUMENTS

| 3,440,320 | A | 4/1969 | Sackler et al. |
| 3,797,494 | A | 3/1974 | Zaffaroni |
| 4,460,372 | A | 7/1984 | Campbell et al. |
| 4,573,996 | A | 3/1986 | Kwiatek et al. |
| 4,624,665 | A | 11/1986 | Nuwayser |
| 4,722,941 | A | 2/1988 | Eckert et al. |
| 4,937,238 | A | 6/1990 | Lemon |
| 5,063,507 | A | 11/1991 | Lindsey et al. |
| 5,130,137 | A | 7/1992 | Crowley, Jr. |
| 5,211,952 | A | 5/1993 | Spicer et al. |
| 5,223,261 | A | 6/1993 | Nelson et al. |
| 5,340,584 | A | 8/1994 | Spicer et al. |
| 5,340,585 | A | 8/1994 | Pike et al. |
| 5,340,586 | A | 8/1994 | Pike et al. |
| 5,468,736 | A | 11/1995 | Hodgen |
| 5,633,242 | A | 5/1997 | Oettel et al. |
| 5,662,927 | A | 9/1997 | Ehrlich et al. |
| 5,827,843 | A | 10/1998 | Koninckx |
| 6,214,815 | B1 | 4/2001 | Shangold et al. |
| 6,500,814 | B1 | 12/2002 | Hesch |
| 7,815,912 | B2 * | 10/2010 | Bunschoten et al. ...... 424/198.1 |
| 7,871,995 | B2 * | 1/2011 | Bunschoten et al. ......... 514/171 |
| 8,026,228 | B2 * | 9/2011 | Coelingh Bennink et al. ............... 514/169 |
| 2002/0183299 | A1 | 12/2002 | Voskuhl |
| 2003/0092628 | A1 * | 5/2003 | de Greef et al. ................ 514/12 |

FOREIGN PATENT DOCUMENTS

| DE | 19917930 A1 | 10/2000 |
| EP | 0402950 A | 12/1975 |
| EP | 468690 A1 | 7/1991 |
| EP | 1700602 A1 | 5/2001 |
| WO | 9603929 A1 | 2/1966 |
| WO | 9426207 | 11/1994 |
| WO | 9502408 A1 | 1/1995 |
| WO | 9517895 | 7/1995 |
| WO | 9603929 A1 | 2/1996 |

(Continued)

OTHER PUBLICATIONS

Hammond et al., "Estetrol does not bind sex hormone binding globulin or increase its production by human HepG2 cells", International Menopause Society, Climateric, vol. 11, (Suppl. 1), pp. 41-46, (2008).
National Institute of Child Health and Human Development, NIH Publication No. 02-2413 retrieved online on Aug. 9, 2007.
Breast Cancer Prevention retrieved online Aug. 7, 2007 from the internet; http://www.cancer.gov/cancertopics/pdq/prevention/breast/Patient/page 3.
Prophylactic definition—Medical Dictionary of Popular Medical Terms; retrieved on Mar. 14, 2008 via www.medterms.com/script/main/art.asp?articlekey+11902.

(Continued)

Primary Examiner — James D Anderson
Assistant Examiner — Bong-Sook Baek
(74) Attorney, Agent, or Firm — The Webb Law Firm

(57) ABSTRACT

The present invention relates to a method of treating infertility in a female mammal that involves controlled ovarian hyperstimulation. The method includes administering to the female a combination of (i) an FSH substance in an amount effective to stimulate follicular development and (ii) a steroid in an effective amount to inhibit or suppress the secretion of luteinising hormone. The steroid can be substances represented by the following formula

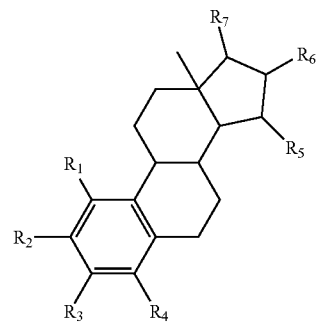

in which formula $R_1$, $R_2$, $R_3$, $R_4$ independently are a hydrogen atom, a hydroxyl group or an alkoxy group with 15 carbon atoms; each of $R_5$, $R_6$, $R_7$ is a hydroxyl group; no more than 3 of $R_1$, $R_2$, $R_3$, $R_4$ are hydrogen atoms; derivatives of the aforementioned steroid substances; or mixtures of one or more of the aforementioned substances or derivatives.

11 Claims, No Drawings

FOREIGN PATENT DOCUMENTS

| | | |
|---|---|---|
| WO | 0062753 | 10/2000 |
| WO | 0073416 A1 | 12/2000 |
| WO | 0130357 A | 5/2001 |
| WO | 0185154 A2 | 11/2001 |

OTHER PUBLICATIONS

Zips et al., in vivo, 2005, vol. 19, pp. 1-8.
Holinka et al., Biology of Reproduction, 1980, vol. 22, pp. 913-926.
Martucci et al., "Impact of Continuously Administered Catechol Estrogens on Uterine Growth and Luteinizing Hormone Secretion", Endocrinology (Dec. 1979), vol. 105, No. 6, pp. 1288-1292.
Weigert et al., "Comparison of Stimulation with Clomiphenes Citrate in Combination with Recombinant Follicle Stimulating Hormone and Recombinant Luteinizing Hormone to Stimulation with a Gonadotropin-Releasing Hormone Agonist Protocol: A Prospective Randomized Study", Fertility and Sterility, (Jul. 2002), vol. 78, No. 1, pp. 34-39.
Trotter et al., "Effects of Postnatal Estradiol and Progesterone Replacement in Extremely Preterm Infants", J. Clin. Endocrinol Metab., (Dec. 1999), vol. 84, No. 12, pp. 4531-4535.
Shanklin et al., "Aqueous Estrogens in the Management of Respiratory Distress SYndrome", J. Reprod. Med. (Aug. 1970), vol. 5, No. 2, pp. 53-71.
Gorwill et al., "Unconjugated Serum Oestriol Levels in Mother and Baby with Meconium Staining of the Amniotic Fluid", Br. J. Obstet. Gynaecol. (Aug. 1978), vol. 85, No. 8, pp. 602-604.
Fogary, Jr., "Postmaturity", J. Am. Osteopath. Assoc., (Jan. 1976), vol. 75, No. 5, pp. 512-517.
Office Action mailed on Jan. 11, 2008 in U.S. Appl. No. 10/478,262.
Office Action mailed on May 15, 2008 in U.S. Appl. No. 10/478,262.
Office Action mailed on Feb. 19, 2009 in U.S. Appl. No. 10/478,262.
Office Action mailed on Jun. 9, 2009 in U.S. Appl. No. 10/478,262.
Office Action mailed on Nov. 18, 2008 in U.S. Appl. No. 10/478,264.
Office Action mailed on May 22, 2009 in U.S. Appl. No. 10/478,264.
Office Action mailed on Mar. 17, 2008 in U.S. Appl. No. 10/478,357.
Office Action mailed on May 16, 2008 in U.S. Appl. No. 10/478,357.
Office Action mailed on Dec. 16, 2008 in U.S. Appl. No. 10/478,357.
Office Action mailed on May 28, 2009 in U.S. Appl. No. 10/478,357.
Office Action mailed on Apr. 6, 2007 in U.S. Appl. No. 10/478,365.
Office Action mailed on Sep. 7, 2007 in U.S. Appl. No. 10/478,365.
Office Action mailed on Apr. 1, 2008 in U.S. Appl. No. 10/478,365.
Office Action mailed on Jun. 8, 2009 in U.S. Appl. No. 10/478,365.
Office Action mailed on Jan. 24, 2007 in U.S. Appl. No. 10/495,707.
Office Action mailed on Dec. 28, 2007 in U.S. Appl. No. 10/495,707.
Office Action mailed on Aug. 19, 2008 in U.S. Appl. No. 10/495,707.
Office Action mailed on May 22, 2009 in U.S. Appl. No. 10/495,707.
Office Action mailed on Oct. 15, 2007 in U.S. Appl. No. 10/517,509.
Office Action mailed on Dec. 19, 2007 in U.S. Appl. No. 10/517,509.
Office Action mailed on Mar. 26, 2008 in U.S. Appl. No. 10/517,509.
Office Action mailed on Jan. 5, 2009 in U.S. Appl. No. 10/517,509.
Office Action mailed on Aug. 18, 2009 in U.S. Appl. No. 10/517,509.
Office Action mailed on Apr. 3, 2007 in U.S. Appl. No. 10/517,686.
Office Action mailed on Aug. 9, 2007 in U.S. Appl. No. 10/517,686.
Office Action mailed on Apr. 4, 2008 in U.S. Appl. No. 10/517,686.
Office Action mailed on May 29, 2009 in U.S. Appl. No. 10/517,686.
Office Action mailed on Apr. 23, 2007 in U.S. Appl. No. 10/521,040.
Office Action mailed on Aug. 17, 2007 in U.S. Appl. No. 10/521,040.
Office Action mailed on Apr. 2, 2008 in U.S. Appl. No. 10/521,040.
Office Action mailed on Jun. 1, 2009 in U.S. Appl. No. 10/521,040.
Visser et al., "In vitro effects of estetrol on receptor binding, drug targets and human liver cell metabolism," Climacteric (2008) 11(1) Appx. II: 1-5.
Visser et al., "First human exposure to exogenous single-dose oral estetrol in early postmenopausal women," Climacteric (2008) 11(1): 1-10.
Visser et al., "Clinical applications of estetrol," J. of Steroid Biochem and Molecular Biol. (2009) 114: 85-89.
Holinka et al., "Estetrol: A unique steroid in human pregnancy," J. of Steroid Biochem and Molecular Biol. (2009) 110: 138-143.
Coelingh Bennink et al., "Oral bioavailability and bone sparing effects of estetrol in an osteoporosis model," Climacteric (2008) 11 (Supp 3): 1-13.
Albertazzi Paola et al., "The Effect of Tibolone Versus Continuous Combined Norethisterone Acetate and Oestradiol on Memory, Libido and Mood of Postmenopausal Women: A Pilot study"; Database Biosis 'Onlinel; Oct. 31, 2000; pp. 223-229; vol. 36, No. 3; Biosciences Information Service, Philadelphia, PA., U.S.
Allen et al., An Ovarian Hormone: Preliminary Report on its Localization, Extraction and Partial Purification, and Action in Test Animals, JAMA, Sep. 8, 1923, vol. 81, pp. 819-821.
Allen et al., The Induction of a Sexually Mature Condition in Immature Females by Injection of the Ovarian Follicular Hormone, Am. J. Physiol., 1924, vol. 69, pp. 577-588.
Jones et al., The Effects of Various Steroids on the Vaginal Histology in the Rat, Fertility and Sterility, Apr. 1973, vol. 24, No. 4, pp. 284-291.
Tulchinsky et al., Plasma Esterol as an Index of Fetal Well-Being, J. Clin. Endrocrinol. Metab., 1975, vol. 40. pp. 560-567.
Jozan et al., Different Effects of Oestradiol, Oestriol, Oestrol and of Oestrone on Human Breast Cancer Cells (MCF-7) in Long Term Tissue Culture, Acta Endocrinologica, 1981, vol. 98, pp. 73-80.
Hammond et al., A Versatile Method for the Determination of Serum Cortisol Binding Globulin and Sex Hormone Binding Globulin Binding Capacities, 1983, vol. 132, pp. 101-110.
Elger et al., Sulfamates of Various Estrogens are Prodrugs with Increased Systemic and Reduced Hepatic Estrogenicity at Oral Application, J. Steroid Biochem. Molec. Biol., 1995, vol. 55, No. 3 / 4, pp. 395-403.
Murphy et al., Endometrial Effects of Long-Term Low-Dose Administration of RU486, Fertility and Sterility, Apr. 1995, vol. 63, No. 4, pp. 761-766.
Reel et al., Survey and Assessment of Mammalian Estrogen Biological Assays for Hazard Characterization, Fundamental and Applied Toxicology, 1996, vol. 34, pp. 288-305.
Beral et al., Use of HRT and the Subsequent Risk of Cancer, Journal of Epidemiology and Biostatistics, 1999, vol. 4, No. 3, pp. 191-215.
Tavani et al., The Adverse Effects of Hormone Replacement Therapy, Drugs & Aging, May 1999, vol. 14, No. 5, pp. 347-357.
Pike et al., Progestins and Menopause: Epidemiological Studies of Risks of Endometrial and Breast Cancer, Steroids, 2000, vol. 65, pp. 359-664.
Avvakumov et al., Steroid-binding Specificity of Human Sex Hormon-binding Globulin is Influenced by Occupancy of a Zinc-binding Site, The Journal of Biological Chemistry, Aug. 25, 2000, vol. 275, No. 34, pp. 25920-25925.
Holinka et al., "In Vivo Effects of Esterol on the Immature Rat Uterus", Biology of Reproduction, Society for the Reproduction Society for the Study of Reproduction, Champaign, IL, US, Mar. 1979, vol. 20, No. 2, pp. 242-246.
Holinka, et al., "Comparison of Effects of Esterol and Tamoxifen with Those of Estriol and Estradiol on the Immature Rat Uterus", Biology of Reproduction, Society for the Reproduction Society for the Study of Reproduction, Champaign, IL, US, 1980, vol. 22, No. 4, pp. 913-926.
Jansson et al., "Estrogen Induces a Potent Suppression of Experimental Autoimmune Encephalomyelitis and Collagen-Induced Arthritis in Mice", Journal of Neuroimmunology, Elsevier Science Publishers BV XX, 1994, vol. 53, No. 2, pp. 203-207.
Erdbruegger et al., Drug Discovery Today: Disease Mechanisms (2004), vol. 1, pp. 73-81.
Lab Tests Online (www.labtestsonline.org/understanding/conditions/autoimmune.html) retrieved on Oct. 15, 2009.
www.tiscali.co.uk/lifestyle/healthfitness/health_advice/netdoctor/archive/000489.html, retrieved on Oct. 15, 2009.
MedlinePlus Medical Encyclopedia: Mutiple Sclerosis, retrieved on Mar. 28, 2008 via www.nlm.nih.gov/medlineplus/ency/article/000737.htm, dated on Aug. 6, 2007, p. 1 and 2; also see WebMD: Multiple Sclerosis—Prevention, retrieved on Mar. 28, 2008 via www.webmd.com/multiple-sclerosis/tc/multiple-sclerosis-ms-prevention, dated on Mar. 23, 2006.
MedlinePlus Medical Encyclopedia: rheumatoid arthritis, retrieved on Mar. 28, 2008 via www.nlm.nih.gov/medlineplus/ency/article/000431.htm, dated on Jul. 27, 2007, p. 1-2 and 4; also WebMD:

Rheumatoid Arthritis—Prevention, retrieved on Mar. 28, 2008 via www.webmd.com/rheumatoid-arthritis/tc/rheumatoid-arthritis-prevention, dated on Aug. 23, 2006.

Mueck et al., "Angio and Anti-Angiogenetic Effects of Estradiol and its Metabolites", J. Clin. Basic Cardiol., 2001, pp. 153-155, vol. 4, No. 2.

Shah et al., "Estrogen and Skin. An Overview", Am. J. Clin. Dermatol., 2001, pp. 143-150, vol. 2, No. 3.

Sitruk-Ware et al., "Local Hormonal Treatment for Urogenital Atrophy After Menopause", Shweiz. Rundsch, Med. Praxis, 1997, pp. 1245-1248, vol. 86, No. 33, and Sitruk-Ware, English Translation, 1997. Praxis, Schweirzerische Rundschau fur Medizin, vol. 86, No. 33, pp. 1-13.

Schmidt et al., "Treatment of Skin Aging with Topical Estrogens", Int. J. Dermatol., 1996, pp. 669-674, vol. 35, No. 9.

Younglai et al., Journal of Clinical Endocrinology and Metabolism, 1968, vol. 28, Issue 11, pp. 1611-1617.

Webster Ninth New Collegiate Dictionary, 2000, Definition of Prevention, p. 1.

Willhite et al., Pharmacotherapy, 2001, vol. 21, Issue 4, pp. 464-480.

Tseng et al., "Heterogeneity of Saturable Estradiol Binding Sites in Nuclei of Human Endometrium. Estetrol Studies", (1978), vol. 9, pp. 1145-1148.

Fishman et al., "Fate of 15 α-Hydroxyestriol-3H in Adult Man", J. Clin. Endocrinol. Metab., (1970), vol. 31, pp. 436-438.

Levine et al., "Uterine vascular effects of estetrol in nonpregnant ewes", Am. J. Obstet. Gynecol., (1984), [148], vol. 73, pp. 735-738.

Martucci et al., "Direction of Estradiol Metabolish as a Control of its Hormonal Action—Uterotrophic Activity of Estradiol Metabolites", Endocrin., (1977), vol. 101, pp. 1709-1715.

Martucci et al., "Uterine Estrogen Receptor Binding of Catecholestrogens and of Estetrol (1,3,5(10)-Estratriene-3, 15a, 16a, 17 β-Tetrol)", Steroids, (1976), vol. 27, pp. 325-333.

Seeger et al., "The inhibitory effect of endogenous estrogen metabolies on copper-mediated in vitro oxidation of LDL", Int. Journal of Clinical Pharmacology and Therapeutics, (1998), vol. 36, No. 7, pp. 383-385.

Tseng et al., "Competition of Estetrol and Ethynylestradiol with Estradiol for Nuclear Binding in Human Endometrium", Journal of Steroid Biochemistry, (1976), vol. 7, pp. 817-822.

Kuipers et al., "Enterohepatic Circulation in the Rat", Gastroenterol., vol. 88, pp. 403-411 (1985).

Schwartz, "A Model for the Regulation of Ovulation in the Rat", Recent Prog. Horm. Res., vol. 25, pp. 1-55, (1969).

Beattie et al., "The Differential Effects of Diestrous Progestogen Administration on Proestrous Gonadotrophin Levels, Endocrinol", vol. 97, pp. 885-890, (1975).

De Visser et al., Endocrinological Studies with (7a, 17 a)-17-Hydroxy-7-me norpregn-5(10)-en-20-yn-3-one (Org OD 14), Arzneim, Forsh., vol. 34, pp. 1010-1020, (1984).

National Cancer Institute: Breast cancer prevention retrieved online Aug. 7, 2007 from the internet; http://www.cancer.gov/templates/doc.aspx?viewed+D972A74B-D25A-4F86-B8ED-33EB3C0450E4&version, p. 1.

Medline Plus: Medical Encyclopedia: Ovarian cancer retrieved online on Aug. 9, 2007 from the internet: https://www.nlm.nih.gov/medlineplus/ovariancancer.html, p. 1 dated Jul. 31, 2007.

Coelingh-Bennink et al., "Estetrol review: profile and potential clinical applications", International Menopause Society, Climateric, vol. 11, (Suppl 1), pp. 47-58 (2008).

White et al., "The pharmacokinetics of Intravenous Estradiol: A Preliminary Study", Pharmacotherapy, vol. 18, pp. 1343-1346, (1998) (Abstract).

* cited by examiner

METHOD OF TREATING OR PREVENTING INFERTILITY IN A FEMALE MAMMAL AND PHARMACEUTICAL KIT FOR USE IN SUCH METHOD

FIELD OF THE INVENTION

The present invention is concerned with a method of treating infertility in a female mammal, e.g. by controlled ovarian hyperstimulation. Another aspect of the invention is concerned with a pharmaceutical kit for use in the present method.

BACKGROUND OF THE INVENTION

The ovarian function of mammalian females is regulated by the hypothalamus and pituitary, secreting gonadotropin releasing hormone (GnRH) and gonadotropins respectively. The gonadotropins are follicle stimulating hormone (FSH), which causes follicle maturation, and luteinising hormone (LH), which causes ovulation.

After each menses, the ovaries are stimulated by FSH released by the pituitary to grow a cohort of follicles. These follicles each comprise an oocyte (egg cell) which is enveloped by an orb of granulosa cells. During growth of the follicles several layers of granulosa cells are being formed. Follicle maturation during the normal menstrual cycle occurs in 12-14 days. Gradually, one follicle becomes dominant and the others become atretic. Maturation of the dominant follicle usually takes 5-7 days. As the number of granulosa cells increases more estrogen is secreted by these cells.

Once the dominant follicle has reached maturity, the follicle will burst (ovulate) under the action of a surge of LH which is released by the pituitary in response to the increased blood serum estrogen level (positive feedback). The oocyte is discharged from the follicle into the ampulla of the Fallopian tube, where fertilization may take place. The oocyte or embryo is transported to the uterus in 5-7 days, where implantation may occur in the midluteal phase.

The follicle that has discharged the oocyte is transformed into a new hormone producing organ, the corpus luteum. The corpus luteum produces amongst others progesterone and estrogens. The corpus luteum has a limited lifespan of about 12-14 days, unless pregnancy occurs. During the second part of that period, it ceases functioning, and as a result the blood level of estrogens and progesterone drops. The decline of progesterone causes shedding of the lining of the uterus and thus menstruation.

In particular in the area of ovulation induction, the past decades have shown the development and commercial introduction of numerous drugs assisting in fertility management of infertile couples. Amongst others, these include anti-estrogens (like clomiphene citrate and tamoxifen citrate), pulsatile GnRH, purified and recombinant gonadotropins, and GnRH agonists and antagonists. The specific drugs used and administration regimens chosen largely depend on the goal of the treatment, e.g. the induction of mono-ovulation in anovulatory females or the controlled ovarian hyperstimulation (COH) to induce multiple follicular development as an element in assisted reproductive technologies (ART). Examples of ART methods that are widely used to treat female and/or male factor infertility include intrauterine insemination (WI) and in vitro fertilization (IVF). IVF can be performed with and without intracytoplasmatic sperm injection (ICSI) and includes a subsequent embryo transfer step.

COH is nowadays widely used in ART. First results with COH were disappointing as a result of the occurrence of premature LH surges in at least 30% of the cases. Such a premature LH-surge may incite ovulation of oocytes and may frustrate harvesting of oocytes for in vitro fertilisation (IVF). It was found that the introduction of GnRH agonists allowed the prevention of premature LH surges as well as programmation of the treatment cycles. To date GnRH agonists are used in most of the cycles. However, GnRH agonists are peptides, requiring parenteral administration, are expensive and are not devoid of adverse effects (long treatment period, side effects, increased incidence of ovarian hyperstimulation syndrome, etc.).

Recently GnRH antagonists were introduced to prevent premature LH surges, to avoid the side effects related to the use of GnRH agonists and to simplify and shorten treatment protocols. However, there are concerns about the pregnancy rates observed with protocols using GnRH antagonists. Several studies have indicated that pregnancy rates for GnRH antagonists are lower than those achieved with GnRH agonists. Furthermore, like GnRH agonist, GnRH antagonists are peptides requiring parenteral administration, which is less favourable.

An area of key interest to IVF-researchers is the poor implantation rate of IVF embryos, responsible for the relatively low implantation rate per embryo. This has lead to the practice of multiple embryo transfers, which practice in turn has lead to high rates of multiple pregnancies. Such multiple pregnancies are considered a major drawback of ART.

As will be apparent from the above there is a need for a method of treating or preventing female infertility which does not employ the aforementioned GnRH analogues, but instead uses a substitute which is equally suitable for preventing premature endogenous LH surges, which produces equal or superior pregnancy rates, can be given orally, gives rise to less side-effects and/or is less expensive.

SUMMARY OF THE INVENTION

It was unexpectedly found that at least a number of the aforementioned requirements are met by a method of treating female infertility that involves COH in which the secretion of LH is inhibited or suppressed by administering an effective amount of a steroid selected from the group consisting of: substances represented by the following formula

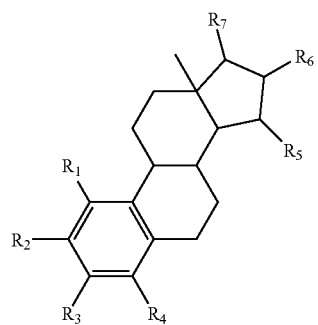

in which formula $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; no more than 3 of $R_1$, $R_2$, $R_3$, $R_4$ are hydrogen atoms;
precursors capable of liberating a substance according to the aforementioned formula when used in the present method; and
mixtures of one or more of the aforementioned substances and/or precursors It was discovered that in a COH-protocol, premature LH-surges may be prevented effectively by administering the aforementioned steroid during the period when the FSH-stimulated (multiple) follicular development may give rise to such a surge.

A typical representative of the present steroids, the human fetal steroid estetrol, interacts with estrogen receptors in a selective manner which is similar to the (tissue) selective receptor interaction of so called Selective Estrogen Receptor Modulators (SERM). Thus, estetrol has more in common with SERMS than with estrogens such as β-estradiol and ethinyl estradiol. In addition, estetrol exhibits a relatively high affinity for the ERα receptor, or conversely a relatively low affinity for the ERβ receptor. It is believed that this receptor specificity is somehow associated with the high efficacy of the present steroids in the suppression of LH-surges, as this kind of receptor specificity has not been observed in known estrogens or SERMs. In view of the SERM-like properties of estetrol and its high ERα affinity, this steroid will be referred to as an 'α-SERM'.

DETAILED DESCRIPTION OF THE INVENTION

Accordingly, one aspect of the present invention relates to a steroid for use in a method of treating infertility in a female mammal that involves COH, said method comprising administering to said female mammal (i) an FSH substance selected from the group consisting of uFSH and recFSH in an amount effective to stimulate follicular development and (ii) a steroid in an effective amount to inhibit or suppress the secretion of luteinising hormone, said steroid being selected from the group consisting of:
substances represented by the following formula:

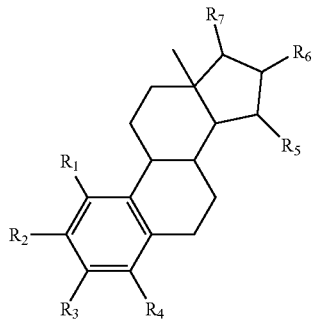

in which formula $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; no more than 3 of $R_1$, $R_2$, $R_3$, $R_4$ are hydrogen atoms;
derivatives of the aforementioned steroid substances wherein the hydrogen atom of at least one of the hydroxyl groups has been substituted by an acyl radical of a hydrocarbon carboxylic, sulfonic or sulfamic acid of 1-25 carbon atoms; tetrahydrofuranyl; tetrahydropyranal; or a straight or branched chain glycosidic residue containing 1-20 glycosidic units per residue; and mixtures of one or more of the aforementioned substances and/or derivatives.

The present steroid substance is special in that the 5 membered ring in the steroid skeleton comprises 3 hydroxyl substituents rather than 0-2.

Preferably, the steroid applied as the active component in the present method is a so called biogenic steroid, i.e. a steroid that occurs naturally in the human body, a precursor (derivative) of a biogenic steroid or a mixture thereof. Because biogenic steroids are naturally present in the human body, side-effects are not expected to occur, particularly not if the serum levels resulting from the exogenous administration of such steroids do not substantially exceed naturally occurring concentrations. Naturally occurring steroids typically exhibit a 8β, 9α, 13β, 14α configuration of the steroid-skeleton.

In a preferred embodiment of the present invention the steroid substance contains 4 hydroxyl groups. Also, in the aforementioned formula, $R_1$ preferably represents a hydrogen atom. In said formula preferably at least 2, more preferably at least 3 of the groups $R_1$, $R_2$, $R_3$ and $R_4$ represent a hydrogen atom.

The steroids according to the formula encompass various enantiomers since the carbon atoms that carry hydroxyl-substituents $R_5$, $R_6$ and $R_7$ are chirally active. In one preferred embodiment, the present steroid substance is 15α-hydroxy substituted. In another preferred embodiment the steroid substance is 16α-hydroxy substituted. In yet another preferred embodiment, the substance is 17β-hydroxy substituted. Most preferably the steroid substances are 15α,16α,17β-trihydroxy substituted.

In a preferred embodiment of the present invention $R_3$ represents a hydroxyl group or an alkoxy group. In another preferred embodiment the groups $R_1$, $R_2$ and $R_4$ represent hydrogen atoms, in which case, if $R_3$, $R_5$, $R_6$ and $R_7$ are hydroxyl groups, the substance is 1,3,5 (10)-estratrien-3,15,16,17-tetrol. A preferred isomer of the latter substance is 1,3,5 (10)-estratrien-3,15α,16α,17β-tetrol (estetrol).

Typical examples of derivatives which can suitably be used in accordance with the invention are esters that can be obtained by reacting the hydroxyl groups of the steroid substances with substances that contain one or more carboxy ($M^+{}^-OOC—$) groups, wherein $M^+$ represents a hydrogen or (akali)metal cation. Hence, in a particularly preferred embodiment, the derivatives of the steroid substances are substances wherein the hydrogen atom of at least one of the hydroxyl groups in said formula has been substituted by —CO—R, wherein R is a hydrocarbon radical comprising from 1-25 carbon atoms. Preferably R is hydrogen, or an alkyl, alkenyl or aryl radical comprising from 1-20 carbon atoms.

The present method may advantageously be employed in the treatment of humans, cattle, sheep, pigs, goat, horses as well as pets such as dogs and cats. Most preferably the present method is employed in humans Good results can be obtained with the present method if the steroid is administered in a daily dosage of less than 10 mg per kg of bodyweight, preferably of less than 5 mg per kg of bodyweight, more preferably of less than 2.5 mg per kg of bodyweight, most preferably of less than 2 mg per kg of bodyweight. In order to achieve significant inhibition or suppression of LH secretion the present steroid is suitably administered in a daily dosage of at least 2.5 µg per kg of bodyweight. Preferably, the administered daily dosage is at least 5 µg per kg of bodyweight. More preferably, the administered daily dosage is at least 10 µg per kg of bodyweight.

In the present method, particularly when used in humans, the steroid is usually administered in a daily dosage of at least 0.125 mg, preferably of at least 0.25 mg, more preferably of at least 0.5 mg, most preferably of at least 1 mg. The maximum daily dosage is normally kept below 500 mg, preferably below 250 mg and more preferably below 125 mg.

The present steroid can be administered in many different ways, i.e. enterally as well as parenterally. The term "parenteral administration" as used in here encompasses transdermal, intravenous, intranasal, intravaginal, pulmonary, buccal, subcutaneous, intramuscular and intra-uterine administration. The term "enteral administration" includes oral as well as rectal administration.

Preferably the mode of administration is selected from the group consisting of oral, transdermal, intravenous, intranasal, intravaginal, pulmonary, rectal, buccal, subcutaneous, intramuscular or intra-uterine administration. More preferably the mode of administration is selected from the group consisting of oral, transdermal, intravenous, subcutaneous, intranasal, pulmonary and vaginal administration. In a particularly preferred embodiment the present method employs oral, transdermal, intranasal or subcutaneous administration. Even more preferably the present method employs oral administration.

The term ML substance encompass substances that display a similar functionality as LH, as well as substances which are capable of triggering the pituitary release of LH.

A particularly preferred embodiment of the present method is a method of controlled ovarian hyperstimulation comprising administration to said female of the steroid in an effective amount to prevent a premature endogenous LH-surge, followed by the administration of a meiosis and luteinisation inducing substance (ML substance) having or inducing luteinising hormone activity in an amount effective to stimulate resumption of meiosis and luteinisation.

The present COH-method is advantageously employed as part of an IVF-protocol. Consequently, in a preferred embodiment, the present method additionally comprises the sequential steps of:

a. harvesting one or more ova from ovarian follicles;
b. fertilising one or more ova in vitro;
c. transferring the resulting embryo into the uterus of a mammalian female.

The embryo may be transferred into the female uterus during the same cycle in which the COH-protocol is applied and the one or more ova are harvested, but it is also possible to transfer the embryo in a subsequent cycle. In a particularly preferred embodiment, the controlled ovarian hyperstimulation and transfer of the embryo are carried out within one cycle.

The term female, whenever referred to in here, relates to mammalian females. Preferably the mammalian female is a *homo sapiens*. For *homo sapiens* females are usually biologically capable of child bearing between the age of 12 and 55.

In a COH protocol it is crucial that administration of the steroid is started sufficiently early to minimise the chance of a premature LH-surge. A reliable indicator of the chance of the occurrence of a premature LH-surge is the size of the developing ovarian follicle, and in particular the size of largest of these developing follicles. Preferably, the steroid is administered at least during the period starting with the moment when the largest developing ovarian follicle has reached an average diameter of 14 mm, preferably of 12 mm, and more preferably of 10 mm, and ending one day prior to the administration of the ML substance in an amount effective to stimulate resumption of meiosis and luteinisation. Usually administration of the steroid will be continued until the moment the ML substance is administered.

To achieve the desired effect on endometrium histology, the steroid is administered at least during the period commencing either 6 days after the start of administration of the FSH substance, or at least 4 days prior to the administration of the ML substance in an amount effective to stimulate resumption of meiosis and luteinisation, whichever is the earliest, and ending one day prior to said administration of the ML substance.

The FSH substance is suitably administered at least during the period starting 8 days after the female's spontaneous menses until the day before administration of the ML substance. More preferably the administration of the FSH-substance is commenced no later than 6 days after the female's menses even more preferably on the second day.

The present method employs a ML substance to stimulate meiosis and luteinisation after the lead follicles have reached maturity and administration of FSH and the present steroid is discontinued. The objective of administering the ML substance at this stage of the cycle is to mimic the LH surge which occurs during the normal menstruation cycle and which induces ovulation, resumption of meiosis and luteinisation. Next to LH a wide range of other pharmaceutical substances may be used to trigger such a response. Preferably the ML substance used in the present method is selected from the group consisting of recombinant LH, urinary chorionic gonadotropin (uCG), recombinant CG, progestogen (including progesterone), gonadotropin releasing hormone (GnRH), GnRH agonists and other substances capable of stimulating the release of LH by the pituitary, chimaeric or otherwise modified gonadotropins with LH-activity, low molecular weight compounds with LH activity and mixtures thereof. More preferably the ML substance is selected from recombinant LH, urinary chorionic gonadotropin (uCG), recombinant CG, gonadotropin releasing hormone (GnRH) and mixtures thereof. The amount of ML substance administered in accordance with the present method preferably is equivalent to a subcutaneous dose of at least 2,000 I.U. urinary chorionic human gonadotropin (uhCG), more preferably to a subcutaneous dose of 5,000-10,000 I.U. uhCG. Preferably the ML substance is administered in a single oral or parenteral dose. Most preferably the ML substance is administered subcutaneously or orally.

It is well known that both FSH and LH may be isolated from female urine. LH isolated from urine is less suitable for use in the present method as it has a very short in vivo half-life ($t_{1/2}$: 10-20 minutes) and is metabolised very quickly. LH obtained from a recombinant cell line (recLH) is much more stable ($t_{1/2}$: 12-13 hours). Consequently, in a particularly preferred embodiment, if LH is used to prevent or suppress symptoms of LH deficiency due to over-suppression, by the steroid, said LH is obtained from a recombinant cell line. The high dose of the ML substance used to stimulate resumption of meiosis and luteinisation is preferably recLH or uhCG (most preferably recLH).

The FSH substance used in the present method is selected from the group consisting of urinary FSH (uFSH) and recombinant FSH (recFSH). As regards uFSH it is noted that this FSH substance can suitably be employed in the form of preparations of urinary origin that besides uFSH also contain urinary LH (uLH) and urinary chorionic gonadotropin (uCG). Although FSH of urinary origin performs almost equally well as recFSH, it is noted that the isolation of active principles from bodily fluids is associated with the risk of transfer of diseases. Hence, in a preferred embodiment, the FSH substance is FSH obtained from a recombinant cell line.

Throughout this document, the term "parenteral administration" encompasses all modes of administration, requiring injection, implantation or topical administration, except for the oral/intestinal route. Suitable examples of parenteral administration include intramuscular, intravenous, subcutaneous, intravaginal, transdermal and intranasal administration.

The FSH substance may suitably be administered parenterally or orally, preferably in an amount that is equivalent to a daily subcutaneous dosage of 1 to 15 I.U. recFSH per kg bodyweight. Most preferably the FSH substance is administered subcutaneously.

As mentioned herein before the present COH-method offers the advantage that it does not require the use of a GnRH agonist or antagonist. However, it is feasible to employ the present steroid in combination with a relatively low dose of antagonist (e.g. between 2 and 20 µg ganirelix per kg bodyweight) so as to reduce the drawbacks associated with the use of such GnRH analogues. Consequently the combined use of the steroid and GnRH analogues is encompassed by the present invention. Preferably, however, no GnRH analogue is employed.

Best results are obtained with the present COH-method if the FSH substance and the LH substance are administered at least once daily. Preferably also the steroid is administered at least once daily.

Another aspect of the present invention relates to a pharmaceutical kit for use in a method of controlled ovarian hyperstimulation in mammalian females, said kit comprising a parenteral dosage unit containing a FSH substance selected from the group consisting of uFSH and recFSH and a parenteral or oral dosage unit containing the steroid. Preferably the kit also comprises a parenteral dosage unit containing an ML substance. Preferably the kit comprises one or two dosage units containing an ML substance. Most preferably the kit comprises one dosage unit containing an ML substance. Preferably the pharmaceutical kit according to the invention comprises the FSH substance in an amount which is equivalent to a subcutaneous dose of between 50 and 1000 IU recFSH, the ML substance in an amount equivalent to a subcutaneous dosage of between 2,000 and 20,000 IU uhCG, the steroid in an amount equivalent to an oral dosage of between 0.1 and 500 mg estetrol.

The parenteral dosage units within the present kit are preferably cartridges for subcutaneous self-administration, containing a sterile liquid formulation.

The present invention is further illustrated by the following examples, which, however, are not to be construed as limiting the scope of the invention. The features disclosed in the foregoing description, in the following examples and in the claims may, both separately and in any combination thereof, be material for realising the invention in diverse forms thereof.

EXAMPLES

Example 1

An open-label, uncontrolled, single centre clinical trial is performed to investigate the efficacy, safety and tolerability of premature LH-surge prevention in 10 women undergoing IVF treatment for infertility by Controlled Ovarian Hyperstimulation (COH), using a daily oral dosage of 40 mg estetrol (E4) from day 6 of FSH treatment up to and including the day of hCG administration to resume meiosis and induce lutëinisation. Oocytes are retrieved 30-38 hours after hCG administration, fertilised in vitro and two days later no more than two embryos are transferred to the uterus of the patient. Standard luteal support is prescribed.

Ultrasonographic monitoring of follicle growth and endometrial thickness are performed during this treatment procedure including extensive and repeated hormonal analysis and measurement of E4 levels extending into the luteal phase after embryo transfer.

A daily oral administration of 40 mg E4 is found to be efficacious in preventing a premature LH-surge and is well tolerated without significant side-effects. Vital pregnancies occur during this new method of COH with oral premature LH-surge prevention.

Example 2

An open-label, randomised, controlled, dose-finding, multi-centre clinical trial is performed to investigate and compare the efficacy, safety and tolerability of premature LH-surge prevention in women undergoing COH/IVF using either E4 in an oral dosage of 1, 5, 10, 20, 40 or 80 mg per day or a daily subcutaneous injection of 0.25 mg ganirelix. Group size is 30 women, so in total 210 patients participate in the trial. E4/ganirelix treatment is started on day 6 of FSH treatment up to and including the day of hCG administration. Further procedures are similar to example 1.

The results show a dose dependent prevention of premature LH-surges with oral E4 with higher dosages being equally effective to parenteral ganirelix. E4 is well tolerated and without significant side-effects. Vital pregnancy rates with E4 show a trend to be superior to ganirelix treated patients.

The invention claimed is:
1. A method of controlled ovarian hyperstimulation in a mammalian female, said method comprising administering to said female a combination of (i) an FSH substance selected from the group consisting of uFSH and recFSH in an effective amount to stimulate follicular development and (ii) a steroid in an effective amount to inhibit or suppress the secretion of luteinising hormone, the steroid being selected from the group consisting of:

substances represented by the following formula

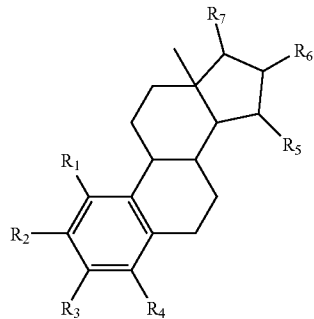

in which formula $R_1$, $R_2$, $R_3$, and $R_4$ independently are a hydrogen atom, a hydroxyl group or an alkoxy group with 1-5 carbon atoms; each of $R_5$, $R_6$, and $R_7$ is a hydroxyl group; no more than three of $R_1$, $R_2$, $R_3$, and $R_4$ are hydrogen atoms;

derivatives of the aforementioned steroid substances wherein the hydrogen atom of at least one of the hydroxyl groups has been substituted by an acyl radical of a hydrocarbon carboxylic, sulfonic or sulfamic acid of 1-25 carbon atoms; tetrahydrofuranyl; tetrahydropyranal; or a straight or branched chain glycosidic residue containing 1-20 glycosidic units per residue; and mixtures of one or more of the aforementioned steroid substances or derivatives.

2. The method according to claim 1, wherein $R_3$ represents a hydroxyl group or an alkoxy group.

3. The method according to claim 1, wherein at least three of $R_1$, $R_2$, $R_3$ and $R_4$ represent hydrogen atoms.

4. The method according to claim 1, wherein the steroid is administered in a daily dose of between 0.5 and 200 mg.

5. The method according to claim 1, wherein the steroid is administered orally.

6. The method according to claim 1, wherein the steroid is administered in an effective amount to prevent a premature endogenous LH-surge.

7. The method according to claim 1, further comprising administering a meiosis and luteinisation inducing substance (ML substance) having or inducing luteinising hormone activity in an amount effective to stimulate resumption of meiosis and luteinisation.

8. The method according to claim 6 further comprising:
a. harvesting one or more ova from ovarian follicles;
b. fertilising one or more ova in vitro;
c. transferring the resulting embryo into the uterus of a mammalian female.

9. The method according to claim 7, wherein the ML substance is selected from the group consisting of recombinant LH, urinary chorionic gonadotropin (uCG), recombinant CG, gonadotropin releasing hormone (GnRH), GnRH agonists and mixtures thereof.

10. A pharmaceutical kit for use in a method of controlled ovarian hyperstimulation in mammalian females, said kit comprising a parenteral or oral dosage unit containing a FSH substance selected from the group consisting of uFSH and recFSH and a parenteral or oral dosage unit containing a steroid selected from the group consisting of:

substances represented by the following formula

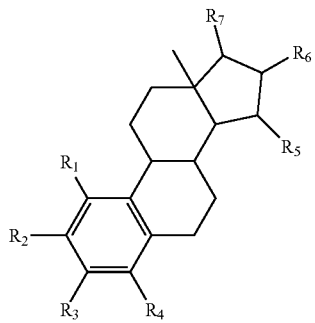

in which formula $R_1$, $R_2$, $R_3$, and $R_4$ independently are a hydrogen atom, a hydroxyl group or an alkoxy group with 1-5 carbon atoms; each of $R_5$, $R_6$, and $R_7$ is a hydroxyl group; no more than three of $R_1$, $R_2$, $R_3$, and $R_4$ are hydrogen atoms;

derivatives of the aforementioned steroid substances wherein the hydrogen atom of at least one of the hydroxyl groups has been substituted by an acyl radical of a hydrocarbon carboxylic, sulfonic or sulfamic acid of 1-25 carbon atoms; tetrahydrofuranyl; tetrahydropyranal; or a straight or branched chain glycosidic residue containing 1-20 glycosidic units per residue; and mixtures of one or more of the aforementioned steroid substances or derivatives.

11. The pharmaceutical kit according to claim 10, wherein the FSH substance is in an amount which is equivalent to a subcutaneous dose of between 50 and 1000 I.U. recFSH.

* * * * *